United States Patent [19]
Liu et al.

[11] Patent Number: 5,462,722
[45] Date of Patent: Oct. 31, 1995

[54] CALCIUM PHOPHATE CACIUM SULFATE COMPOSITE IMPLANT MATERIAL

[76] Inventors: Sung-Tsuen Liu, 29 Landing, Laguna Niguel, Calif. 92677; Harvey H. Chung, 43 Via Costa Verde, Rancho Palos Verdes, Calif. 90274

[21] Appl. No.: 687,592

[22] Filed: Apr. 17, 1991

[51] Int. Cl.⁶ .......................... C01B 15/16; C01B 25/26; C01F 11/46; A61F 2/28
[52] U.S. Cl. .......................... 423/311; 423/305; 423/306; 423/307; 423/555; 623/16
[58] Field of Search .................. 424/422, 423; 623/16; 423/306, 311, 555, 305, 307

[56] References Cited

U.S. PATENT DOCUMENTS 1,357,120  10/1926  Sadtler ........................... 423/306
4,843,112  1/1989   Gerhart et al. ..................... 523/114

FOREIGN PATENT DOCUMENTS 9100252  1/1991  WIPO ..................................... 623/16
9117722  11/1991 WIPO ..................................... 623/16

Primary Examiner—Thurman K. Page
Assistant Examiner—Carlos Azpuru
Attorney, Agent, or Firm—Drucker & Sommers

[57] ABSTRACT

This invention provides new inorganic composite materials for hard tissue replacement. The new composite material comprises solid material of calcium sulfate which is fully or partially converted to calcium phosphate from aqueous solution. This composite material has good biocompatibility and controllable resorption, and will be very useful for bone substitute material in orthopaedic and dental applications. The fully converted material which comprises mainly apatite calcium phosphate is also useful for chromatography application. A process to prepare these new composite materials is also described.

14 Claims, No Drawings

CALCIUM PHOPHATE CACIUM SULFATE COMPOSITE IMPLANT MATERIAL

FIELD OF INVENTION

The present invention relates to a bone substitute material and a method of production thereof.

DESCRIPTION OF THE PRIOR ART

In orthopaedic surgery and dental applications, there is a great need for biocompatible and bioresorbable implant materials which can be used as a bone substitute. This includes bone lost due to periodontal disease, ridge augmentation, bone defect or bone cavities due to trauma or surgery, and spinal fusion. After implantation, the bone substitute is resorbed and replaced by the formation of new bone.

In orthopaedic surgery, autogenous bone has been used quite often for bone repair or bone substitute. Autogenous bone has good biocompatibility, is not subject to immunological rejection, and induces bone growth. However, it requires a secondary surgery and thus increases the burden on the patient while delaying recovery. On the other hand, both homogeneous bone from other human sources and heterogeneous bone from animal sources always suffer the disadvantages of adverse immunological reactions. This will result in an inflammatory reaction and rejection after implantation.

The major inorganic composition of hard tissue is a calcium phosphate compound called biological apatite. Bone has 65% to 70% of biological apatite and teeth contain near 98% biological apatite. Hydroxyapatite and other apatite compounds have the same crystal structure as biological apatite. In principle, these apatite materials should be ideal candidates for bone replacement. However, the precipitated hydroxyapatite and other apatite compounds have very fine particle size. The difficulty in manipulating these fine powders renders them useless as materials for bone replacement.

Recently, many attempts have been made to prepare artificial bone substitute materials. Among these are metal, plastics and ceramics. In the past, several types of ceramics have been developed. These included aluminum oxide, calcium sulfate dihydrate, a glass containing calcium phosphate, and a variety of calcium phosphate ceramics.

The advancement of ceramics technology to prepare different types of calcium phosphate ceramics makes the medical application of calcium phosphate realized. In fact, clinical studies confirmed that apatite ceramic has the best biocompatibility among the artificial bone substitutes. Other calcium phosphate compounds or ceramics such as dicalcium phosphate, tricalcium phosphate, octacalcium phosphate and tetracalcium phosphate also show excellent biocompatibility.

Previous studies indicated that dense hydroxyapatite is not bioresorbable, while porous β-tricalcium phosphate and other calcium phosphates are bioresorbable. The bioresorption rate of β-tricalcium phosphate is rather difficult to predict. Plaster of Paris has been studied as a hard tissue replacement material for many years. In general, Plaster of Paris has acceptable biocompatibility. However, its resorption rate is too fast to match the ingrowth of new bone formation. In orthopaedic surgery, particularly in bone defect repair, there is a great need for an implant material with good biocompatibility and a controllable resorption rate.

SUMMARY OF THE INVENTION

The present invention provides a new calcium phosphate and calcium phosphate-calcium sulfate composite for hard tissue implant. While precipitated calcium phosphate from aqueous solution is very fine and cannot be used for medical application, this invention provides a technique which can produce calcium phosphate and calcium phosphate-calcium sulfate composites from aqueous solution of any size and shape suitable for medical application.

This invention includes using a suitable and desired size and shape of calcium sulfate as starting material, and converts this calcium sulfate to calcium phosphate by aging in phosphate ion containing solution at high pH and high temperature. During the conversion process the crystal size and shape of the starting material is retained, and the reaction occurs from the outside of the particle and toward the inside of the calcium sulfate crystal.

The conversion rate depends principally on phosphate ion concentration, pH, temperature of the solution and particle size and shape of calcium sulfate used. Normally, the conversion rate will increase by raising pH, increasing temperature, increasing phosphate ion concentration and decreasing the particle size of the starting calcium sulfate crystal.

The required time of aging depends strongly on the degree of conversion one wants and the conversion rate. It also depends on the phosphate ion content in the solution. Therefore, the aging time may be predetermined. The conversion process is shown diagrammatically as follows:

DIAGRAM 1.

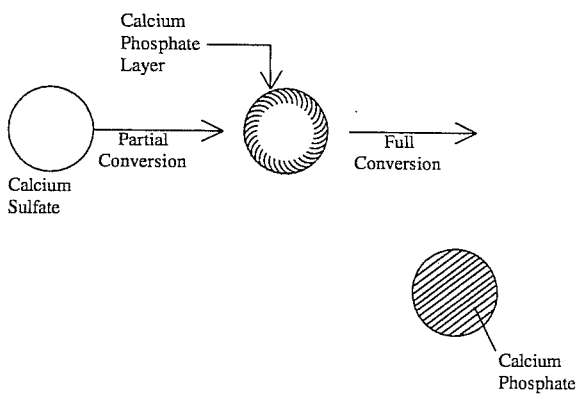

DESCRIPTION OF THE PREFERRED EMBODIMENT

A new hard tissue implant material of calcium phosphate and calcium phosphate-calcium sulfate composite is made from calcium sulfate crystals. By "aging" calcium sulfate crystals of particles in a high pH and phosphate ion containing solution at high temperature, they will convert completely or partially to calcium phosphate but still retain their original particle size and shape.

The conversion reaction occurs from the surface of the calcium sulfate particle first, and the reaction continues inwardly (See DIAGRAM 1). The conversion rate as well as the degree of conversion depends strongly on the concentration of phosphate ion, solution pH and temperature, particle size and the original shape of calcium sulfate crystal.

In general, the increase of phosphate ion concentration and the decrease of particle size will favor the conversion rate.

Both the calcium phosphate salt resulting from full conversion and calcium phosphate-calcium sulfate composite resulting from partial conversion are suitable materials for hard tissue replacement.

The above implantation materials of this invention may be made as follows: An aging solution is prepared by dissolving water-soluble phosphate salts and enough ammonium hydroxide or alkali hydroxides to make a solution pH of at least 10 and preferably 11 or greater. The solution is then preheated to at least 70° C. (preferably at 80° C. and higher), and maintained at the same temperature during the aging process. The starting calcium sulfate materials comprises the powder, granule or block form of calcium sulfate, and said starting material is then aged in the above solution for a predetermined time period.

The required aging time depends strongly on the degree of conversion wanted and the rate of conversion. The conversion rate will vary with solution pH, temperature and the particle size of calcium sulfate. For example, a complete conversion of calcium sulfate, having a particle size smaller than 300 microns, to calcium phosphate may take only 9 hours or less in an excess phosphate ion containing solution having a pH=12, at 90° C. Under these pH and temperature conditions, a much shorter time is required to obtain the partially converted product. However, it would take a much longer time to complete the conversion for a large block form of calcium sulfate at a lower pH and lower temperature.

Preferred water soluble phosphate salts for preparation of the aging solution are sodium phosphate, potassium phosphate and ammonium phosphate, and preferred alkali hydroxides for pH adjustment are sodium hydroxide and potassium hydroxide.

The calcium sulfate starting material may be any one of a variety of calcium sulfate materials such as calcium sulfate dihydrate, calcium sulfate hemihydrate, or calcium sulfate anhydrous. The starting calcium sulfate material may be prepared by reacting 500 ml of 2M calcium chloride solution with equal molar sulfuric acid solution at room temperature. After reaction, the precipitated solid is filtered and washed several times with deionized water. The precipitate formed comprises calcium sulfate dihydrate in needle shaped crystals. Crystals of calcium sulfate dihydrate with other crystal morphology and particle size, may be prepared under other precipitating conditions well known in the art, and may also be used.

A starting material of calcium sulfate hemihydrate crystal may also be prepared by heating calcium sulfate dihydrate crystals prepared as above, at temperatures ranging from 160° C. to 190° C. Insoluble calcium sulfate anhydrous crystals are prepared by calcination of the calcium sulfate dihydrate crystals at temperatures above 400° C.

Calcium sulfate dihydrate, calcium sulfate hemihydrate or calcium sulfate anhydrous materials with larger particle sizes are prepared by the following processes: Calcium sulfate hemihydrate crystals are first mixed with enough water to form a paste. After several minutes, the paste hardens. This hardened paste is calcium sulfate dihydrate. The hardened paste is then broken into the desired particle size of calcium sulfate dihydrate. The hemihydrate paste can also be molded to any shape before hardening, resulting in a molded shape of calcium sulfate dihydrate. Larger particle sizes of calcium sulfate hemihydrate and calcium sulfate anhydrous crystals may then be prepared from the above prepared calcium sulfate dihydrate by thermal treatment or calcination.

The more compact calcium sulfate anhydrous is prepared by conventional ceramic techniques. Fine calcium sulfate dihydrate, hemihydrate, or anhydrous particles are compressed to first form "green cake." The "green cake" is then sintered at 1000° C. to 1200° C. to form a calcium sulfate ceramic. These molded calcium sulfate ceramics are then broken into the desired particle size of calcium sulfate anhydrous ceramics. The molded calcium sulfate anhydrous ceramics as well as the desired size of calcium sulfate anhydrous ceramics are further treated with phosphate ion containing solution, as earlier set forth, to prepare the composite materials for bone substitution.

Any of the foregoing calcium sulfate forms may be used as starting material for this invention. The calcium sulfate chosen is then partially or fully converted to a calcium phosphate in the presence of a phosphate ion containing solution at a pH of 10 or greater, and at temperatures of 70° C. or greater, as earlier described. After conversion, the particles still retain the original particle size and shape of the calcium sulfate starting material.

Most of the calcium phosphate ceramics or calcium phosphate containing bioglass[1] require time to adjust their surface for bone interaction with body fluids after implantation. On the other hand, the calcium phosphate and/or calcium sulfate-calcium phosphate composite material formed by this invention are closer to biological apatite in nature. Therefore, they are more compatible for bone interaction.

[1] A bioactive glass material whose major components are CaO, $SiO_2$ and $P_2O_5$. Minor components may be $Na_2O$, MgO, $Al_2O_3$, $B_2O_3$ and $CaF_2$. A bioactive glass can form a surface layer of hydroxyapatite when soaked in the aqueous environment.

In summary, the present bone substitute provides a calcium phosphate surface which is very close to biological apatite. It is also well known that bone remodeling and bioresorption occur more rapidly beginning several weeks after implantation. Thereafter, the bioresorption activity decreases sharply. The present bone substitute will also provide the advantage of controlling the bioresorption rate by providing a two phase composite of calcium phosphate-calcium sulfate. A further advantage of the present invention is that one can prepare calcium phosphate compounds from aqueous solution with any desired particle size suitable for implantation.

EXAMPLE 1

20 g of calcium sulfate hemihydrate was mixed with 9 ml of pure water to form a slurry. The slurry was then stirred homogeneously. After the mixed paste was set, the set material was then broken into particles. Particle sizes of between 40 to 60 mesh and between 20 to 40 mesh were then collected. After the collected particles were completely dried, 5 g of the respective particles were weighed. Two separate glass flasks were filled with 50 ml of water. To each of the glass flasks was added 5.5 g of $(NH_4)_2HPO_4$ and the solution pH was maintained at 10 or higher by adding ammonium hydroxide. The solution was then heated to 80° C., and 5 g of each of the above prepared calcium sulfate dihydrate samples was added to the flask. The calcium sulfate dihydrate suspension was then "aged" at 80° C. or higher for about twelve hours with occasional stirring, during which time period, the starting material is converted to a calcium phosphate material. After that, the suspension was filtered and the separated solid particles were washed with pure water and air dried. The dried solid was checked by microscopic observation.

The results showed that the particles retained their original crystal shape. By solution test with 0.1M HCl, the final solid dissolved more readily than the original calcium sulfate dihydrate indicating substantially full conversion of calcium sulfate dihydrate to calcium phosphate during the aging process. X-ray analysis also confirmed the conversion reaction.

EXAMPLE 2

Fine crystals of calcium sulfate dihydrate were prepared by adding sulfuric acid to an equal molar lime suspension. After the reaction was completed, the precipitated suspensions were filtered, and the solid was then washed with pure water several times. The precipitated fine calcium sulfate dihydrate solids were then lubricated with steric acid and compressed in cylinder form. The compressed cylinder form of calcium sulfate dihydrate "green cake" was then sintered at temperatures ranging from 1000° to 1200° C. The sintered calcium sulfate anhydrous ceramic was then ground. Calcium sulfate ceramic particle sizes of between 20 to 40 mesh were collected. 16 g of $(NH_4)_2HPO_4$ was added to a 200 ml flask containing 100 ml of water. The ammonium phosphate solution was then heated to 80° C. or higher, and the pH of the solution was kept at 10 or higher by adding ammonium hydroxide. 10 g of the prepared calcium sulfate anhydrous ceramics was then "aged" in the above ammonium phosphate solution for a period of about 12 hours. During the aging process, the suspension was stirred occasionally and the temperature of the solution was maintained at 80° or higher. Thereafter, the solid suspension was filtered. The filtered solid was then washed several times with pure water and air dried.

The final solids dissolved readily in strong acid solution in comparison with the original calcium phosphate ceramics indicating full conversion to calcium phosphate salt. Similar conversion results can be obtained by using sodium phosphate, potassium phosphate, lithium phosphate or cerium phosphate solution at high temperatures of 80° C. or higher with a solution pH at 10 or higher.

EXAMPLE 3

In order to get partially converted calcium sulfate, two approaches can be employed. The first method is by controlling the reaction time. For example, by keeping other conditions the same as in Example 1 and 2, but reducing the aging time to one hour, the resulting calcium sulfate dihydrate or calcium sulfate anhydrous ceramic showed only a partial conversion to the apatite form of calcium phosphate.

The second method is to control the Ca/phosphate mole ratio in the solution. In examples 1 and 2 the calcium to phosphate mole ratio is less than 1.5 and full conversion to calcium phosphate occurred. When the calcium to phosphate mole ratio in examples 1 and 2 was increased to greater than 1.5 (e.g. 1.67) by reducing the corresponding phosphate content, the resulting solid shows only a partial conversion to calcium phosphate under the same process conditions. If the reaction time is sufficiently long, then the degree of conversion again depends on the mole ratio of calcium to phosphate.

EXAMPLE 4

In examples 1 to 3, the full or partial conversion of calcium sulfate dihydrate and calcium sulfate anhydrous to calcium phosphate has been demonstrated. Calcium sulfate hemihydrate can also be converted to calcium phosphate. However, the aging temperature should be kept near 95° C. or higher. A phosphate containing solution was prepared by dissolving 10 g of $Na_2HPO_4$ or $Na_3PO_4$ in a 200 ml flask containing 100 ml of water with pH adjusting to 10 or higher by using sodium hydroxide. The phosphate solution was then heated to 95° C. or higher and maintained at this temperature. 10 g of fine calcium sulfate hemihydrate crystal was then added into the phosphate containing solution and aged with occasional stirring for 12 hours. At the end of aging, the solids were separated by filtration and washed several times with pure water. The resulting crystals maintained the original crystal morphology but were almost completely converted to calcium phosphate.

The fully converted product of calcium phosphate may be successfully used in chromatographic separation of proteins and polypeptides, in orthopaedic surgery, in maxillofacial surgery, as a bone graft and as a bone filler. The partially converted product of calcium phosphate-calcium sulfate composite may be used in orthopaedic surgery, in maxillofacial surgery and as bone graft material.

The method herein, for making a calcium phosphate article, also includes selecting a desired particle size of calcium sulfate, then fabricating an implantable object from said calcium sulfate particles, and adding said object to an aqueous alkaline solution of a phosphate salt, having a temperature of at least 70° C. and a pH of at least 10, for a sufficient period of time to at least partially convert said calcium sulfate article to calcium phosphate.

The phosphate salt(s) can be replaced by phosphoric acid, so long as the pH is maintained at about 10 or higher.

It should be understood that the foregoing disclosure emphasizes certain specific embodiments of the invention and that all modifications or alternatives equivalent thereto are within the spirit of scope of the invention.

I claim:

1. A method for converting a particle of calcium sulfate, having a desired size and shape, into a particle of one of a calcium phosphate and calcium phosphate-calcium sulfate composite for use in hard tissue replacement, comprising:

preparing a particle of calcium sulfate having a desired size and shape;

preparing an aqueous alkaline solution of a phosphate salt having a pH of at least 10;

preheating and maintaining said aqueous alkaline solution temperature to at least 70° C. or higher; and adding said particle of calcium sulfate to said preheated aqueous alkaline solution and permitting reaction to occur for a time period effective to effectuate the substitution of at least some of the calcium sulfate of said particle with calcium phosphate, and thereby to obtain a product selected from a fully converted product of calcium phosphate and a partially converted product of a calcium phosphate-calcium sulfate composite.

2. The method of claim 1 wherein the particle of calcium sulfate is selected from the group consisting of calcium sulfate dihydrate, calcium sulfate hemihydrate and calcium sulfate anhydrous.

3. The method of claim 1 wherein the particle of calcium sulfate is selected from the group consisting of a powder form, a granule form, a sintered form, and a block form of calcium sulfate.

4. The method of claim 1 wherein said phosphate salt is selected from the group consisting of ammonium phosphate, sodium phosphate, potassium phosphate, lithium phosphate and cerium phosphate.

5. The method of claim 1 wherein said phosphate salt is replaced by phosphoric acid.

6. The method of claim 1 wherein said aqueous alkaline solution includes an alkali hydroxide selected from the group consisting of sodium hydroxide, potassium hydroxide, and ammonium hydroxide.

7. The method of claim 1 wherein the pH is at least 10 or higher.

8. The method of claim 1 wherein solution temperature is maintained at least 80° C. during said reaction.

9. The method of claim 1 wherein the mole ratio of calcium to phosphate in said preheated alkaline solution, after addition of said calcium sulfate, is less than 1.5 in order to obtain a fully converted calcium phosphate product.

10. The method of claim 1 wherein the mole ratio of calcium to phosphate in said preheated alkaline solution, after addition of said calcium sulphate, is more than 1.5 in order to obtain said partially converted calcium phosphate-calcium sulfate composite product.

11. The method of claim 1 wherein said fully converted product of calcium phosphate and said partially converted product of calcium phosphate-calcium sulfate composite retain their original particle size and shape.

12. The method of claim 1 wherein said calcium phosphate-calcium sulfate composite has a calcium phosphate outer layer and a calcium sulfate inner layer.

13. A method of making a calcium phosphate article, which is formed of calcium phosphate particles, for implantation, from an article having the same size and shape, but which is formed of calcium sulfate particles, comprising:

selecting a particle size of calcium sulfate that is the same as that utilized for said calcium phosphate article;

fabricating an implantable object from the said calcium sulfate particles; and adding said object for implantation to an aqueous alkaline solution of a phosphate salt, having a temperature of at least 70° C. and a pH of at least 10, for an effective period of time to cause at least some of said calcium sulfate particles to be transformed into particles of calcium phosphate, and thereby at least partially convert said calcium sulfate article to a calcium phosphate article.

14. The method of claim 3 wherein the mesh size of the said granule form of calcium sulfate lies between about 300 mesh and 10 mesh.

* * * * *